(12) United States Patent
Rudzinski et al.

(10) Patent No.: US 6,448,451 B1
(45) Date of Patent: Sep. 10, 2002

(54) PROCESS FOR REMOVAL OF DIMETHYL ETHER IN THE SYNTHESIS OF SEVOFLURANE

(75) Inventors: Ralph Rudzinski, Martinsville; Ralph Lessor, New Providence, both of NJ (US)

(73) Assignee: Baxter International, Inc., Deerfield, IL (US)

( * ) Notice: Subject to any disclaimer, the term of this patent is extended or adjusted under 35 U.S.C. 154(b) by 0 days.

(21) Appl. No.: 09/874,346

(22) Filed: Jun. 5, 2001

(51) Int. Cl.$^7$ ................................................ C07C 41/34
(52) U.S. Cl. ........................................ 568/682; 568/683
(58) Field of Search ................................. 568/682, 683

(56) References Cited

U.S. PATENT DOCUMENTS

| | | | |
|---|---|---|---|
| 3,352,928 A | 11/1967 | Gilbert et al. | 260/633 |
| 3,476,860 A | 11/1969 | Croix et al. | 424/342 |
| 3,527,814 A | 9/1970 | Croix et al. | 260/614 |
| 3,689,571 A * | 9/1972 | Regan et al. | 514/816 |
| 4,874,902 A | 10/1989 | Huang et al. | 568/683 |
| 5,886,239 A | 3/1999 | Kudzma et al. | 568/684 |

\* cited by examiner

*Primary Examiner*—Rosalynd Keys
(74) *Attorney, Agent, or Firm*—Dechert

(57) ABSTRACT

The invention provides a process for purifying methyl 2,2,2-trifluoro-1-(trifluoromethyl)ethyl ether, comprising: passing a composition comprising methyl 2,2,2-trifluoro-1-(trifluoromethyl)ethyl ether and dimethyl ether through an evaporation zone; evaporating dimethyl ether by passing a gas stream through the composition; and removing the gas comprising dimethyl ether from the composition.

20 Claims, 1 Drawing Sheet

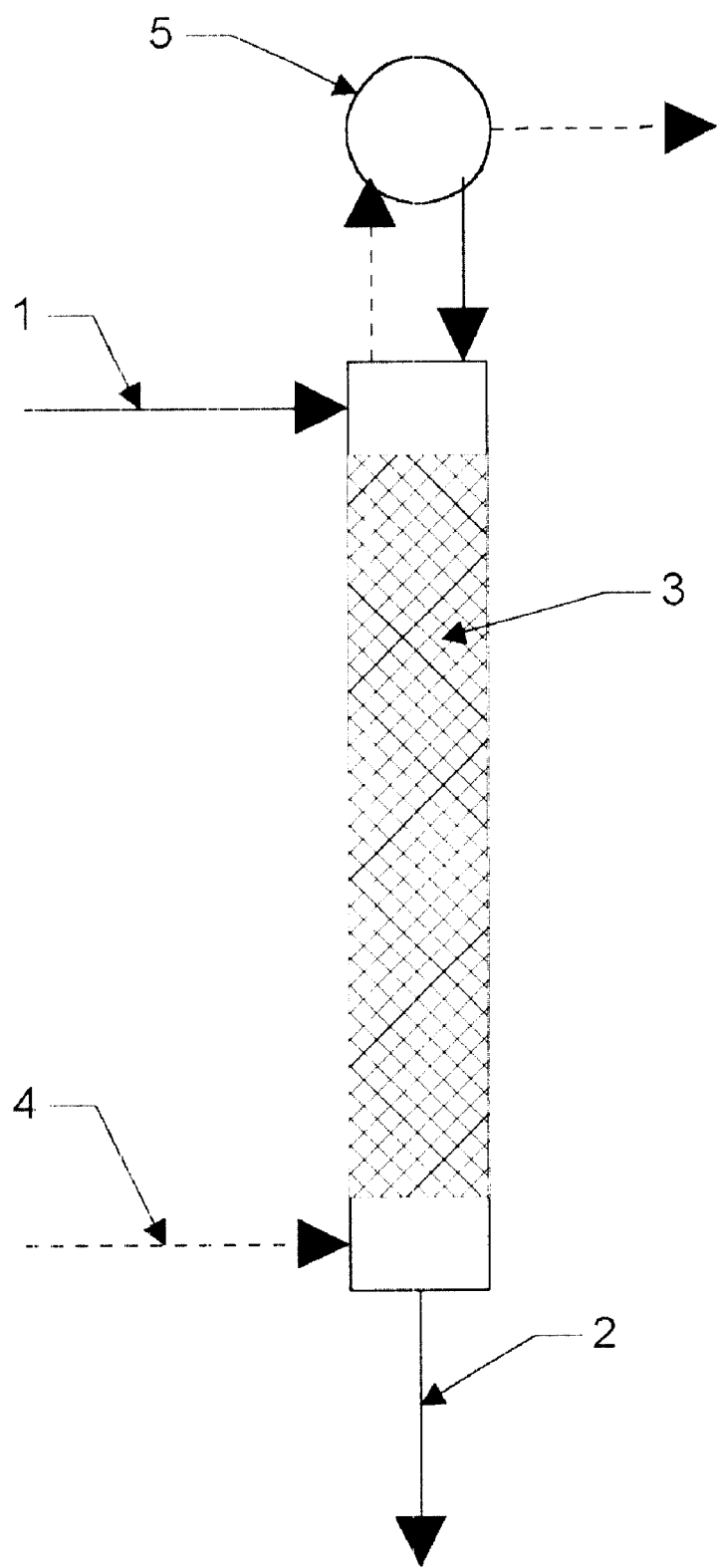

PROCESS FOR REMOVAL OF DIMETHYL ETHER IN THE SYNTHESIS OF SEVOFLURANE

The present invention relates to a process of purifying methyl 2,2,2-trifluoro-1-(trifluoromethyl)ethyl ether, an intermediate in the synthesis of fluoromethyl 2,2,2-trifluoro-1-(trifluoromethyl)ethyl ether (sevoflurane). More specifically, the invention relates to a process for removing dimethyl ether from an intermediate used in a preferred synthesis of sevoflurane. Using the methods of the invention the safety, efficiency, and yield of the sevoflurane synthetic process are improved.

In recent years, fluorinated ethers have been discovered which have useful anesthetic properties. Included among these is sevoflurane ($(CF_3)_2CHOCH_2F$). Sevoflurane is an advantageous inhalation anesthetic because it provides for rapid onset of anesthesia and rapid recovery. Sevoflurane is administered by the inhalation route to warm-blooded animals in an amount of from about 1% to 5% by volume in admixture with oxygen or a gaseous mixture containing oxygen in an amount sufficient to support respiration.

A preferred process for preparing sevoflurane consists of the three-step process that is depicted in Scheme 1. In the first step, reaction of 1,1,1,3,3,3-hexafluoro-2-propanol (HFIP) with dimethyl sulfate in the presence of base provides methyl 2,2,2-trifluoro-1-(trifluoromethyl)ethyl ether in high yields. Second, the ether can then be treated in a photochemical chlorination procedure to provide chloromethyl 2,2,2-trifluoro-1-(trifluoromethyl)ethyl ether. In the third step, the chloromethyl ether from the second step is reacted with a nucleophilic fluoride source, such as a tertiary amine hydrofluoride salt, to displace of the chlorine with fluoride ion and provide sevoflurane.

Scheme 1

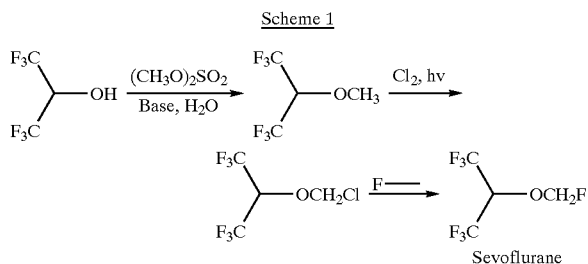

U.S. Pat. Nos. 3,683,092 and 3,689,571 disclose the method of the first step of producing methyl 2,2,2-trifluoro-1-(trifluoromethyl)ethyl ether by reaction of HFIP with dimethyl sulfate. This reaction provides a high yield of the desired product, together with a small amount of HFIP, which can be removed from the desired product by washing with aqueous sodium hydroxide solution.

The washed product contains dimethyl ether (up to about 2% by weight under certain conditions), which forms as a by-product by reaction of methanol (formed by base catalyzed hydrolysis of dimethyl sulfate) with dimethyl sulfate. In addition, dimethyl ether in the reagent dimethyl sulfate can further contribute to contamination of the desired product.

While dimethyl ether itself is not particularly hazardous (although it is very flammable), by-products formed from contaminating dimethyl ether in subsequent synthetic steps impose problematic handling and purification burdens in the synthesis of sevoflurane. Specifically, dimethyl ether, if present, can be chlorinated in the second synthetic step forming various chlorinated dimethyl ether species that contaminate the desired intermediate, chloromethyl 2,2,2-trifluoro-1-(trifluoromethyl)ethyl ether.

One of the chlorinated dimethyl ether compounds which may be produced as a by-product in the second step is bis-chloromethyl ether ($ClCH_2OCH_2Cl$). As chlorinated dimethyl ethers are halogenated organics, regulatory concerns often mandate costly hazardous waste disposal procedures. Moreover, contaminating dimethyl ether species interfere with the purification of later process intermediates and in the purification of sevoflurane, itself Finally, chlorinated dimethyl ethers, if present in the third chemical step of the preferred process, can react to form chlorofluoro ethers. Such chlorofluoro ethers require the burdensome disposal procedures that have been mentioned above for halogenated organics. Chlorofluoro ethers are problematic sevoflurane product contaminants.

What is needed are new processes for removing dimethyl ether from sevoflurane processes that assure high purities of process intermediates and subsequently produced sevoflurane. Processes for dimethyl ether removal are preferably economical and convenient to implement in manufacturing processes.

SUMMARY OF THE INVENTION

In one embodiment, the invention relates to a process for purifying methyl 2,2,2-trifluoro-1-(trifluoromethyl)ethyl ether. In the process, a composition having methyl 2,2,2-trifluoro-1-(trifluoromethyl)ethyl ether and dimethyl ether is passed through an evaporation zone. Dimethyl ether is evaporated by passing a gas stream through the composition, and the gas containing dimethyl ether is removed from the composition. The evaporation zone is heated in certain embodiments of the process. Preferably, the temperature of the evaporation zone is from about 60 to 80° C. In preferred embodiments at this evaporation zone temperature, the pressure of the evaporation zone is from about 15 to 25 psig.

In yet another embodiment, the invention relates to a process for preparing fluoromethyl 2,2,2-trifluoro-1-(trifluoromethyl)ethyl ether. In this process, 1,1,1,3,3,3-hexafluoro-2-propanol and dimethyl sulfate can be reacted to provide a composition containing methyl 2,2,2-trifluoro-1-(trifluoromethyl)ethyl ether and dimethyl ether. Methyl 2,2,2-trifluoro-1-(trifluoromethyl)ethyl ether can be purified by passing the composition through an evaporation zone, evaporating dimethyl ether by passing a gas stream through the composition, and removing the gas containing dimethyl ether from the composition. The purified methyl 2,2,2-trifluoro-1-(trifluoromethyl)ethyl ether can be chlorinated to provide chloromethyl 2,2,2-trifluoro-1-(trifluoromethyl) ethyl ether. This chloromethyl ether can then be treated with a nucleophilic fluoride source to obtain fluoromethyl 2,2,2-trifluoro-1-(trifluoromethyl)ethyl ether.

BRIEF DESCRIPTION OF THE DRAWINGS

FIG. 1 displays one embodiment of an apparatus useful for removing dimethyl ether impurity from compositions containing methyl 2,2,2-trifluoro-1-(trifluoromethyl)ethyl ether.

DETAILED DESCRIPTION OF THE INVENTION

In accordance with the present invention a process is provided for the efficient removal of dimethyl ether from compositions containing methyl 2,2,2-trifluoro-1-(trifluoromethyl)ethyl ether.

Using the methods of the present invention, it has been found that dimethyl ether can be removed with surprising efficiency and convenience from compositions containing methyl 2,2,2-trifluoro-1-(trifluoromethyl)ethyl ether and dimethyl ether. The advantages realized by practicing the methods of the invention include significant impacts on safety, cost, time and labor in the synthesis of sevoflurane.

The preferred three-step procedure for the synthesis of sevoflurane discussed above includes the steps of: (1) methylation of HFIP; (2) chlorination of the resulting methyl ether; and (3) fluoride treatment of the intermediate chloromethyl ether. The methods of the present invention are particularly well-suited to removing the dimethyl ether impurity from compositions containing the methyl 2,2,2-trifluoro- 1-(trifluoromethyl)ethyl ether (also known as sevoflurane methyl ether or SME) obtained from step (1). However, the invention can be practiced without limitation as to the source of the compositions.

The process of the invention includes preferentially evaporating the dimethyl ether impurity and other low-boiling components, such as those found in small amounts in the starting materials, while maintaining the bulk of the SME in the liquid state. An illustrative apparatus for conducting the process is shown schematically in FIG. 1. There is an evaporation zone that is adapted to increase the surface area of the feed stock while passing a gas through the evaporation zone to create preferably multiple areas or stages where vapor and liquid compositions are in equilibrium. In the device of the illustrative Figure, there is a feed conduit 1, an effluent conduit 2, a bed packed with a high surface area support 3, a gas input 4, and an optional condenser 5. Components in the gaseous phase are depicted by hatched arrows, while components in the liquid phase are depicted by solid arrows.

Dimethyl ether is efficiently removed by a passing a gas stream through an evaporation zone containing a composition of SME and dimethyl ether. The gas entrained with the dimethyl ether impurity is carried up through a series of equilibrium stages and is enriched in dimethyl ether until it leaves the area where liquid and vapor are in equilibrium.

Evaporation zones are defined by apparatuses that increase the surface area of a liquid composition containing SME and dimethyl ether. The evaporation zones create "equilibrium stages" where vapor is kept in intimate contact with the liquid. As recognized by those of ordinary skill in the art, an "equilibrium stage" (also known as an "ideal stage" or "theoretical stage") is a segment where, under the operating parameters of the apparatus, a contact between a liquid phase and a vapor phase of sufficient time that the vapor and liquid phases leaving the "stage" are in equilibrium. The increase in surface area can be accomplished by any appropriate device as will be recognized by those of ordinary skill in the art. A preferred number of equilibrium stages used is six or greater.

In one embodiment, an evaporation zone is a zone provided with a gas stream into which the liquid composition containing SME and dimethyl ether is sprayed or atomized through appropriate nozzles. The zone into which the liquid is sprayed into can be heated, or alternatively, the feedstream containing the liquid composition can be heated.

In yet another embodiment, the evaporation zone is a zone where the composition containing SME and dimethyl ether is refluxed or warmed under an efficient condenser (optionally through a packed column of material) while passing a gas stream through the apparatus. The gas stream is preferably introduced through the surface of the heated liquid and is allowed to flow through the evaporation zone.

In a preferred embodiment of the invention, the evaporation zone is a tubular apparatus filled with a material of high surface area permitting close contact of liquid and vapor. For instance, distillation columns that are packed with granular or mesh supports serve as effective evaporation zones. Packing materials for the distillation columns preferably are chemically inert materials that simultaneously provide high surface area and low resistance to liquid and gas flow. Goodloe column packing, for example, a structured wire mesh packing commercially available from Metex Corporation, is a preferred column packing material. Other column packing materials include Raschig rings; glass beads or helices; metal rings, helices or beads; or beads, rings, helices or mesh of chemically inert polymer materials such as poly(tetrafluoroethylene) and the like. In addition, columns having articulations that increase the surface area that are formed integral with the peripheral walls, such as Vigreux columns can be used in combination with packed columns. Columns are preferred evaporation zones for embodiments of the invention suitable for larger scale continuous manufacturing processes. Typical column sizes include columns having diameters of from about four inches to about three feet and heights of from about five to about 50 feet.

Using columns with packing materials as evaporation zones, the liquid composition containing SME and dimethyl ether is percolated through the packing material at a flow rate that is, in one embodiment, less than the flooding rate, such as less than 80% of the flooding rate. In some embodiments, however, the liquid composition can be percolated through the column at rates greater than the flooding rate if the partially purified liquid is then recirculated through the packed column to further purify the composition (e.g., by pumping the partially purified liquid composition to the column inlet). Thus, multiple passes of the liquid composition through the packed column at rates greater than the flooding rate can also effectively remove dimethyl ether and other low-boiling component to provide purified SME.

In some embodiments, the evaporation zone can be connected to a condenser. A condenser mounted at the top of the evaporation zone returns condensed, at least partially purified SME (i.e., the condensate contains reduced levels of dimethyl ether relative to the vapor from which it is condensed) to the evaporation zone. In alternative embodiments, the condensate can be collected in a separate vessel for recycling, or it can be discarded. The temperature of the condenser zone or other areas within the evaporation zone can be controlled to maximize dimethyl ether removal and SME recovery. The effluent vapors, enriched in dimethyl ether, that pass through the condenser zone can be recovered, scrubbed, or otherwise disposed of.

The process can be run in a batchwise or continuous manner. In the batchwise process, the feed of crude composition can take place at a point other than the top of the evaporation zone.

The product SME with significantly reduced levels of dimethyl ether can be collected at the bottom of the evaporation zone. Preferably, the collected SME from the process contains less than 0.05 weight % dimethyl ether, more preferably less than 0.005 weight %. The collected SME can be analyzed by any method known to those ordinary skill in the art. For example, the collected SME can be analyzed by gas chromatography or $^1$H NMR analysis to assess its purity. Preferably, the recovery of SME is at least 95%.

The collected SME from the process of the invention can be used, without further purification, in step (2) of the preferred sevoflurane process, i.e., the chlorination reaction. In preferred embodiments the evaporation zone is heated to increase the rate of dimethyl ether removal. Preferably, the zone is heated to a temperature that maximizes the evaporation of the dimethyl ether impurity while maintaining the bulk of the SME in the liquid state. For example, in an evaporation zone that includes a packed column, the column can be heated by an external heat source, e.g., an electric heating coil or steam jacket. The evaporation zone such as a packed column is preferably maintained at from about 60 to 80° C. Alternatively, the source of the heat can be provided by heating the gas used to evaporate the dimethyl ether. Another source of heat, useful for laboratory scale processes, is provided by refluxing the composition containing the SME and dimethyl so that the volatilized composition warms the evaporation zone. Preferably, the liquid stream providing feed composition to the evaporation zone is also temperature controlled. For example, in embodiments where the composition is sprayed into a vacant space to increase its surface area, the liquid composition can be heated prior to spraying.

The pressure of the evaporation zone can be varied to optimize the efficiency of the dimethyl ether removal process. Preferably, the removal process is run at slightly elevated pressures such as from about 5 to 150 psi to maximize the recovery of the desired SME entrained in the effluent gas stream. More preferably the removal process is run at pressures from about 15 to 25 psi. Preferably, the evaporation zone temperature is from about 60° C. to about 80° C., with the pressure in the evaporation zone from about 15 to 25 psi. At higher pressures it has been found that the mole fraction of the SME in the effluent stream is reduced, thereby increasing the recovery of the SME.

The gas used in the dimethyl ether removal process can be any gas that is chemically inert toward SME, dimethyl ether, or other components also present in the composition. Due to the flammability of dimethyl ether, the gas used is preferably a traditional inert gas such as nitrogen, argon, or helium. More preferably the inert gas used is nitrogen.

The rate of the gas flow can be controlled to optimally balance the factors of increased rate of dimethyl ether removal and minimization of the SME loss to evaporation. It has also been found that it is advantageous to introduce the gas stream at the bottom of the evaporation zone while providing an outlet for the effluent stream at the top of the zone.

Additional components such as water can be present in the composition so long as they do not interfere with the removal of dimethyl ether. For instance, residual amounts of water remaining in the organic layer after aqueous extraction steps are not harmful to the process. Such extraction steps can be applied in workup procedures of the reaction mixture obtained from the methylation of HFIP.

The methods of the invention render rapid and efficient purification of the sevoflurane intermediate, SME. Moreover, the chlorinated dimethyl ether species, formed in the subsequent chlorination reaction, are either avoided or their concentrations are significantly reduced. The costly handling procedures associated with chlorinated dimethyl ether species are thereby avoided or greatly minimized. The advantages attributable to the invention significantly improve the sevoflurane manufacturing process.

The following example further illustrates the present invention, but of course, should not be construed as in any way limiting its scope.

EXAMPLE 1

Purification of Methyl 2,2,2-trifluoro-1-(trifluoromethyl)ethyl ether

A stream of methyl 2,2,2-trifluoro-1-(trifluoromethyl) ethyl ether containing 6793 ppm of dimethyl ether was fed at 135 lbs/h to the top of a 6 in. diameter column packed with 25 ft of Goodloe stainless steel wire mesh packing. Steam was fed to a heat exchanger at the bottom of the column to maintain the temperature in the middle of the column at about 65° C. to 75° C. A stream of nitrogen was fed into the bottom of the column at 4 standard ft$^3$/h. The pressure of the column was maintained at 20 psig. The product, collected from the bottom of the column contained 6 ppm of dimethyl ether.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A process for purifying methyl 2,2,2-trifluoro-1-(trifluoromethyl)ethyl ether, comprising:

passing a composition comprising methyl 2,2,2-trifluoro-1-(trifluoromethyl)ethyl ether and dimethyl ether through an evaporation zone, evaporating dimethyl ether by passing a gas stream through the composition ; and removing the gas stream comprising dimethyl ether from the composition.

2. The process of claim 1, wherein the temperature of the evaporation zone is from about 60 to 80° C.

3. The process of claim 2, wherein the pressure of the evaporation zone is from about 15 to 25 psig.

4. The process of claim 3, wherein the gas is an inert gas.

5. The process of claim 1, wherein the evaporation zone is heated.

6. The process of claim 1, further comprising a condensing zone adapted to condense at least a portion of any methyl 2,2,2-trifluoro-1-(trifluoromethyl)ethyl ether in the removed gas and return the condensed methyl 2,2,2-trifluoro-1-(trifluoromethyl)ethyl ether composition to the evaporation zone.

7. The process of claim 1, wherein the evaporation zone comprises at least six equilibrium stages.

8. The process of claim 7, wherein the temperature of the evaporation zone is from about 60 to 80° C.

9. The process of claim 8, wherein the pressure of the evaporation zone is from about 15 to 25 psig.

10. The process of claim 1, wherein the evaporation zone comprises a granular or mesh support.

11. The process of claim 10, wherein the evaporation zone comprises a mesh support of structured wire mesh.

12. The process of claim 1, wherein the composition of methyl 2,2,2-trifluoro-1-(trifluoromethyl)ethyl ether dimethyl ether is prepared by reaction of 1,1,1,3,3,3-hexafluoro-2-propanol and dimethyl sulfate.

13. The process of claim 1, wherein the composition is passed through the evaporation zone by injecting it through one or more atomizing or spray nozzles.

14. The process of claim 1, wherein there is less than 0.05 wt. % of dimethyl ether in the purified methyl 2,2,2-trifluoro-1-(trifluoromethyl)ethyl ether.

15. The process of claim 1, wherein the recovery of purified methyl 2,2,2-trifluoro-1-(trifluoromethyl)ethyl ether is at least 95%.

16. A process for purifying methyl 2,2,2-trifluoro-1-(trifluoromethyl)ethyl ether, comprising:

passing a composition comprising methyl 2,2,2-trifluoro-1-(trifluoromethyl)ethyl ether and dimethyl ether through an evaporation zone, wherein the evaporation zone has a temperature of from about 60 to 80° C. and a pressure of from about 15 to 25 psig;

evaporating dimethyl ether by passing an inert gas stream through the composition; and removing the inert gas stream comprising dimethyl ether from the composition.

17. The process of claim 16, wherein the evaporation zone comprises a granular or mesh support.

18. The process of claim 17, wherein the evaporation zone comprises a mesh support of structured wire mesh.

19. A process for preparing fluoromethyl 2,2,2-trifluoro-1-(trifluoromethyl)ethyl ether, comprising:

(a) reacting 1,1,1,3,3,3-hexafluoro-2-propanol and dimethyl sulfate to provide a composition comprising methyl 2,2,2-trifluoro-1-(trifluoromethyl)ethyl ether and dimethyl ether;

(b) purifying methyl 2,2,2-trifluoro-1-(trifluoromethyl)ethyl ether from the composition of (a) by a process comprising:

passing the composition through an evaporation zone, evaporating dimethyl ether by passing a gas stream through the composition, and removing the gas stream comprising dimethyl ether from the composition;

(c) chlorinating the purified methyl 2,2,2-trifluoro-1-(trifluoromethyl)ethyl ether to provide chloromethyl 2,2,2-trifluoro-1-(trifluoromethyl)ethyl ether; and (d) reacting chloromethyl 2,2,2-trifluoro-1-(trifluoromethyl)ethyl ether with a nucleophilic fluoride source to obtain fluoromethyl 2,2,2-trifluoro-1-(trifluoromethyl)ethyl ether.

20. The process of claim 19, wherein the composition from step (a) is extracted with water and the extracted composition is purified in step (b).

* * * * *